US012013387B2

(12) United States Patent
Sequeira et al.

(10) Patent No.: US 12,013,387 B2
(45) Date of Patent: Jun. 18, 2024

(54) DETERMINING RESERVOIR FLUID COMPOSITION TO PENTATETRACONTANES PLUS

(71) Applicant: Saudi Arabian Oil Company, Dhahran (SA)

(72) Inventors: Daryl Sean Sequeira, Dhahran (SA); Ahmed M. Sahl, Dammam (SA); Okechukwu M. Egbukole, Al-Khobar (SA)

(73) Assignee: Saudi Arabian Oil Company, Dhahran (SA)

( * ) Notice: Subject to any disclaimer, the term of this patent is extended or adjusted under 35 U.S.C. 154(b) by 568 days.

(21) Appl. No.: 17/198,535

(22) Filed: Mar. 11, 2021

(65) Prior Publication Data

US 2022/0290560 A1  Sep. 15, 2022

(51) Int. Cl.
*G01N 33/28* (2006.01)
*G01N 30/68* (2006.01)
(Continued)

(52) U.S. Cl.
CPC ......... *G01N 33/2823* (2013.01); *G01N 30/68* (2013.01); *G01N 30/8665* (2013.01);
(Continued)

(58) Field of Classification Search
CPC ............... G01N 30/8665; G01N 30/68; G01N 33/2823; G01N 2030/025;
(Continued)

(56) References Cited

U.S. PATENT DOCUMENTS

| 8,522,600 B2 | 9/2013 | Al-Eid et al. |
| 8,991,233 B2 | 3/2015 | Kriel et al. |
| 2012/0085149 A1 | 4/2012 | Al-Eid et al. |

FOREIGN PATENT DOCUMENTS

| CA | 2823711 A1 * | 7/2012 | .......... H01J 49/0031 |
| WO | WO-2009142873 A1 * | 11/2009 | ............. E21B 43/00 |

OTHER PUBLICATIONS

PCT International Invitation to Pay Additional Fees and, Where Applicable, Protest Fees in International Appln. No. PCT/US2022/019762, dated May 23, 2022, 13 pages.
(Continued)

*Primary Examiner* — Benjamin R Schmitt
(74) *Attorney, Agent, or Firm* — Fish & Richardson P.C.

(57) ABSTRACT

Methods and a system for determining a composition of a fluid from a reservoir are provided. An exemplary method includes depressurizing a single-phase fluid to atmospheric pressure to separate a gas phase from a liquid phase, recording the volume of the gas phase, determining the weight of the liquid phase, and determining an atmospheric gas-oil ratio (GOR) from the volume of the gas phase and the weight of the liquid phase. The method also includes determining the composition of the gas phase to C9+, measuring the density of the liquid phase, determining the molecular weight of the liquid phase, and determining the composition of the liquid phase to C45+. The total hydrocarbon composition of the fluid is calculated from the amount of the gas phase, the amount of the liquid phase, the composition of gas phase, the composition liquid phase, and the atmospheric GOR.

9 Claims, 6 Drawing Sheets

(51) Int. Cl.
*G01N 30/86* (2006.01)
*G01N 30/02* (2006.01)
*G01N 30/06* (2006.01)
*G01N 30/88* (2006.01)

(52) U.S. Cl.
CPC .. *G01N 2030/025* (2013.01); *G01N 2030/062* (2013.01); *G01N 2030/8854* (2013.01)

(58) Field of Classification Search
CPC ...... G01N 2030/062; G01N 2030/8854; E21B 49/08; E21B 49/086; E21B 49/087; E21B 49/080875
See application file for complete search history.

(56) References Cited

OTHER PUBLICATIONS

Sequeira et al., "A Novel Approach to Determine Reservoir Fluid Composition from Separator Test Data." SPE Annual Technical Conference and Exhibition. OnePetro, Sep. 2021, 12 pages.
ASTM International, "Standard Test Method for Analysis of Natural Gas by Gas Chromatography" Reapproved 2019, Designation D1945-14, Dec. 2019, 17 pages.
ASTM International, "Standard Test Method for Boiling Range Distribution of Petroleum Fractions by Gas Chromatography" Designation D2887-19A, Dec. 2019, 35 pages.
PCT International Search Report and Written Opinion in International Appln. No. PCT/US2022/019762, dated Jul. 15, 2022, 18 pages.

* cited by examiner

300

DETERMINING RESERVOIR FLUID COMPOSITION TO PENTATETRACONTANES PLUS

TECHNICAL FIELD

The present disclosure is directed to techniques for determining reservoir fluid composition from pressurized fluid from a well.

BACKGROUND

Obtaining accurate and reliable reservoir fluid composition is essential to petroleum upstream operations. Conventional methods such as distillation, direct flash and gas chromatographic techniques to determine reservoir fluid composition proved to be challenging due limitations in extended gas chromatographic analysis and liquid carryover into gas phase. In addition, the ability to identify and quantify the concentrations of oil-based mud (OBM) and generate decontaminated composition proved to be challenging due to the presence of complex mixtures of oil-based drilling fluids in contaminated fluids.

Reservoir fluid composition has often been analyzed to heptanes plus (C7+) fraction or dodecanes plus (C12+) fractions using low temperature fractional distillation and gas chromatographic techniques. Subsequently, methods such as direct flash in combination with gas chromatograph to obtain fluid composition to eicosanes plus fraction (C20+), tricontanes plus (C30+), and hexatriacontanes plus (C36+) fractions have replaced fractional distillation

SUMMARY

An exemplary embodiment method for determining a composition of a fluid from a reservoir. The method includes depressurizing a single-phase fluid to atmospheric pressure to separate a gas phase from a liquid phase, recording the volume of the gas phase, determining the weight of the liquid phase, and determining an atmospheric gas-oil ratio (GOR) from the volume of the gas phase and the weight of the liquid phase. The method also includes determining the composition of the gas phase to C9+, measuring the density of the liquid phase, determining the molecular weight of the liquid phase, and determining the composition of the liquid phase to C45+. The total hydrocarbon composition of the fluid is calculated from the amount of the gas phase, the amount of the liquid phase, the composition of gas phase, the composition liquid phase, and the atmospheric GOR.

Another exemplary embodiment described in examples herein provides a method for measuring a composition of a reservoir fluid. The method includes pressurizing a sample container holding the reservoir fluid to form a single-phase fluid, pumping the single-phase fluid from the sample container into a separation oven, releasing pressure on the single-phase fluid in a flashing container to form a liquid phase and a gas phase, capturing the liquid phase in the flashing container, and flowing the gas phase through a gas collection cylinder into tubing in a gas accumulator oven. The method also includes recirculating a portion of the gas phase through the liquid phase at atmospheric pressure to equilibrate components in the gas phase and components in the liquid phase, and capturing a sample of the gas phase in the gas collection cylinder.

Another embodiment described in examples herein provides a direct flash separator system. The direct flash separator system includes a separation oven. The separation oven includes a liquid flash container, a flash gas sample container, and a recirculation pump. The direct flash separator system also includes a gas accumulation oven. The gas accumulation oven includes a copper tubing line, a gas capture valve, and a digital gas meter.

DETAILED DESCRIPTION

Figure 2:
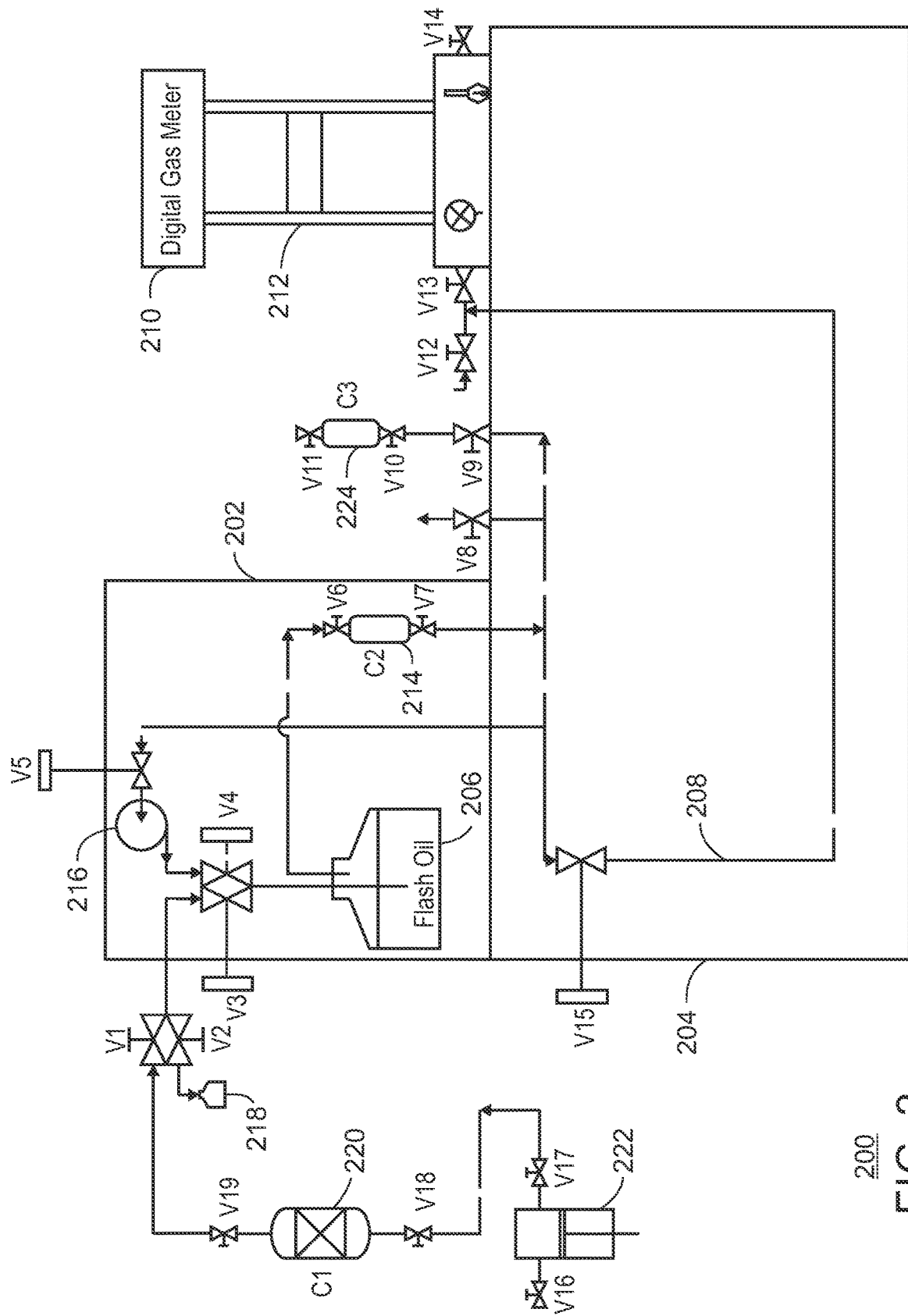
FIG. 2 is a simplified process diagram of a direct-flash separator system

The techniques described herein provide for the determination of reservoir oil composition of pressurized fluids to pentatetracontanes plus (C45+) by resolving petroleum fractions into distinct boiling point fraction. A direct flash, utilizing the direct flash separator system described with respect to FIG. 2, is used to segregate a flashed liquid, termed a liquid phase herein, and a flashed gas, termed a gas phase herein. The ratio of the phases are used to generate an atmospheric gas-oil ratio (GOR). Gas chromatography is then used to analyze the composition of the phases. The information obtained from the gas chromatography analyses are combined with other information collected, such as the GOR, to determine the reservoir oil composition to a C45+ fraction. The techniques described have provided reliable and repeatable higher molecular weight compositions and improved estimation of the oil-based mud (OBM) content in the fluid. Further, the technique can also be used for heavy oils.

In the technique, a portion of single-phase pressurized fluid is flashed to atmospheric pressure at a specified temperature, e.g., between about 20° C. and about 60° C., to be separated into gas and liquid phases for further evaluation. The volume of the gas phase is recorded and its composition determined to C9+ using an extended chromatographic technique. The weight, density, and molecular weight of the liquid phase are measured. The composition of the liquid phase is determined to C45+ using high-resolution gas chromatographic technique. The relative amounts of gas and liquid phases and their compositions are then recombined mathematically with the measured atmospheric gas-oil ratio (GOR) to obtain the total hydrocarbon oil composition to C45+ in terms of weight percent and mole percent.

Figure 1:
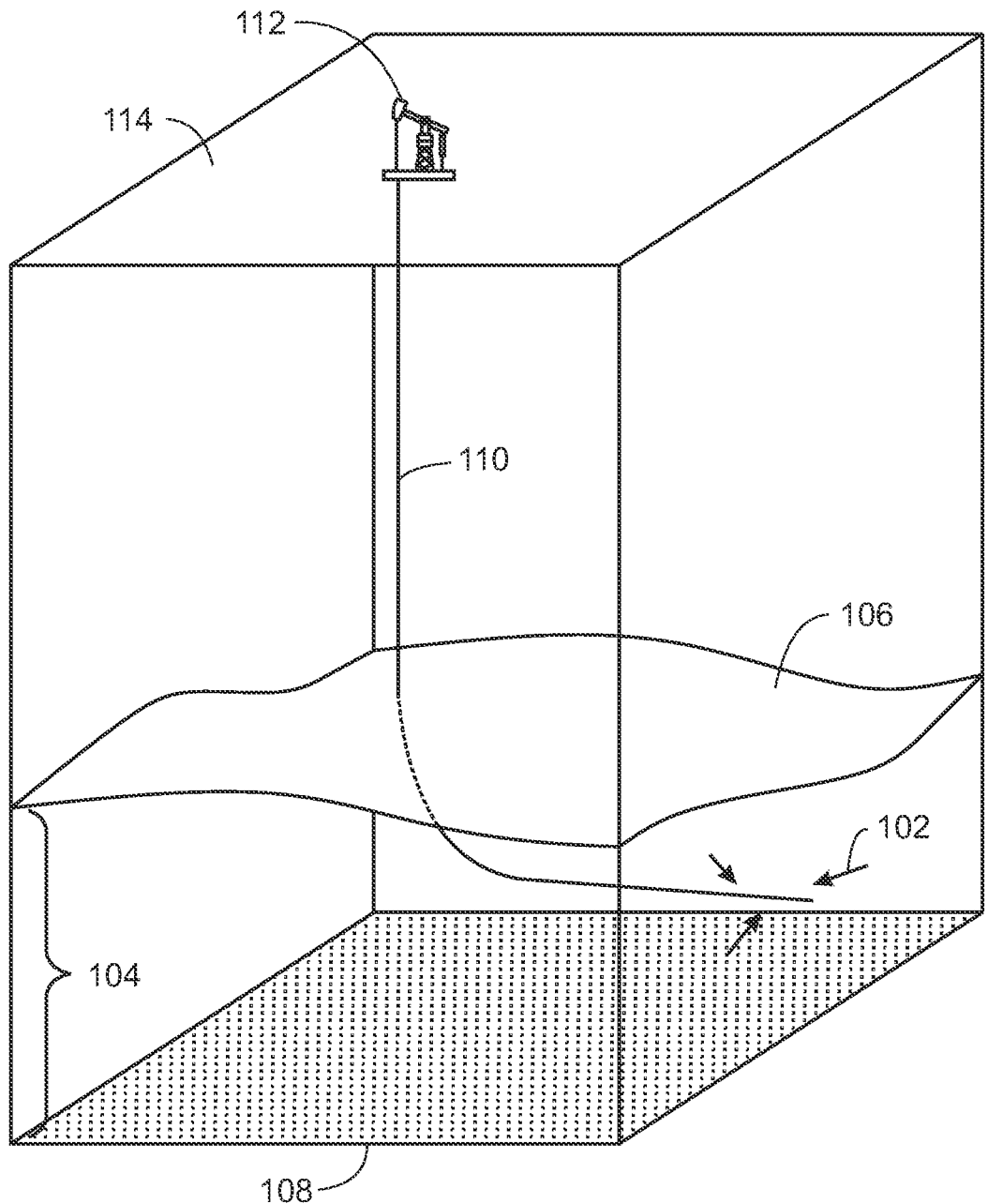
FIG. 1 is a schematic drawing of the production of hydrocarbons from a reservoir layer.

FIG. 1 is a schematic drawing 100 of the production of hydrocarbons 102 from a reservoir layer 104. In this example, the reservoir layer 104 is captured between a cap rock layer 106 and an aquifer 108. The reservoir layer 104 is produced through a wellbore 110, for example, using a pump 112 at the surface 114.

Generally, the hydrocarbons 102 in the reservoir layer 104 are not evenly distributed, but are located in areas of higher concentration, termed reservoirs. Accordingly, the wellbore 110 is often directionally drilled to reach the reservoirs in the reservoir layer 104. Fluid composition data is important for the management and development of reservoirs within the reservoir layer 104, for example, helping to locate reservoirs in the reservoir layer 104 and to develop plans for producing the reservoirs.

Increasing the accuracy of the composition of the hydrocarbons from the reservoir may improve the location and production plans, enabling a higher amount of hydrocarbons to be recovered. Accordingly, extending the determination of reservoir oil composition to C45+ fractions is useful. The extended fluid composition data will allow robust equations-of-state (EOS) to be developed for use in simulation software to predict reservoir fluid properties. Further, for reservoir fluids that are contaminated with complex mixtures of oil-based mud (OBM) drilling fluids, the techniques will improve the accuracy of mathematical correction methods. These techniques, such as skimming and subtraction, may be used to identify and quantify the concentration of oil-based mud (OBM) and calculate decontaminated composition.

FIG. 2 is a simplified process diagram of a direct-flash separator system 200. The system includes two ovens. A top or separation oven 202 and a bottom or gas accumulation oven 204. A glass flask 206 collects the liquid phase from the fluid sample. Tubing 208, such as copper tubing, in the gas accumulation oven 204 collects the gas phase. A digital gasometer 210 mounted on an aluminum frame 212 is used to measure the volume of the gas phase.

A gas collection cylinder (C2) 214 is located with the glass flask 206 in the separation oven 202. This allows the gas collection cylinder 214 to directly capture the flashed gas phase during the experiment for reservoir fluids exhibiting low bubble point pressure (such as less than 100 psi) and low gas-oil ratio (such as less than 50 scf/bbl).

A circulation pump (CP) 216 is also included in the separation oven 202. The CP 216 is used to recirculate the gas phase, for example, through the gas collection cylinder 214 and through the liquid phase in the glass flask 206 to bring the composition of the gas and liquid phases to equilibrium before composition analysis.

The flows in the direct-flash separator system 200 are controlled by two-way valves. These include the 2-way valve V1-V2. The valve V2 is utilized to bleed sample to check for sample quality. In addition, V2 can be utilized to measure H2S concentration in the gas phase, for example, using a gas detector 218 available from Gastech of Wangara, Western Australia. An additional 2-way valve, V3-V4, is used for sampling or recirculation of the gas phase through the liquid phase. The valve V4 is utilized to recirculate flash gas through the flash liquid phase once the experimentation is completed by closing V3.

The fluid sample is provided to the direct-flash separator system 200 in a sample cylinder 220. The sample cylinder 220 is a pressurized fluid piston cylinder that allows a driving fluid entering through V18 to move a piston, increasing the pressure of a sample fluid above the piston without the driving fluid contacting the piston. A positive displacement pump 222 is used to provide the driving fluid for increasing the pressure in the sample cylinder 220 to form a single-phase sample, and then force the single-phase sample into the separation oven 202. The single-phase sample is then flashed across V3 into the glass flask 206.

In various embodiments, all wetted parts of the direct-flash separator system 200 are treated to be resistant to sulfur chemicals, for example, using coatings technology such as the Sulfinert® coatings available from SilcoTek® of Bellefonte, PA, USA, among others. In various embodiments, the glass flask has a volume of 100 mL, and the flash gas cylinder, or gas collection cylinder 214, has a volume of 75 mL.

Generally, the bottom oven, or gas accumulation oven 204, is set to a temperature of 75° C., while the temperature in the top oven, or separation oven 202, is set between about 20° C. and about 60° C. based on the API and waxy nature of the crude oil or reservoir fluid sample. For example, for a reservoir fluid sample with an API between about 25 and about 60, the separation oven 202 temperature would be set to about 20° C. or ambient laboratory temperature. For a reservoir fluid sample with an API of less than about 25, the separation oven 202 temperature would be set to between about 50° C. and about 60° C. For a waxy reservoir fluid sample, the separation oven temperature would be set to between about 40° C. and about 60° C.

In various embodiments, the volume of the tubing 208 in the gas accumulation oven 204, e.g., between valves V15 and V12/V13, is about 10 L. In some embodiments, the volume of the recirculation system in the separation oven 202, e.g., including tubing connections, valves V3-V4, V5, V6, V7, V8, V9, and V15, glass flask 206, and the gas collection cylinder 214, is about 350 mL.

The direct-flash separator system 200 is not limited to the components described above. In some embodiments, the components may be sized differently depending on the amount of sample available. For example, if very little sample is available a smaller glass flask 206 and gas collection cylinder 214 may be used. In these embodiments, a smaller volume of tubing 208 may also be used. In some embodiments, an additional gas collection cylinder 224 may be coupled to the tubing 208 for taking samples directly from the tubing 208, e.g., without equilibration with the liquid phase in the glass flask 206.

Figure 3:
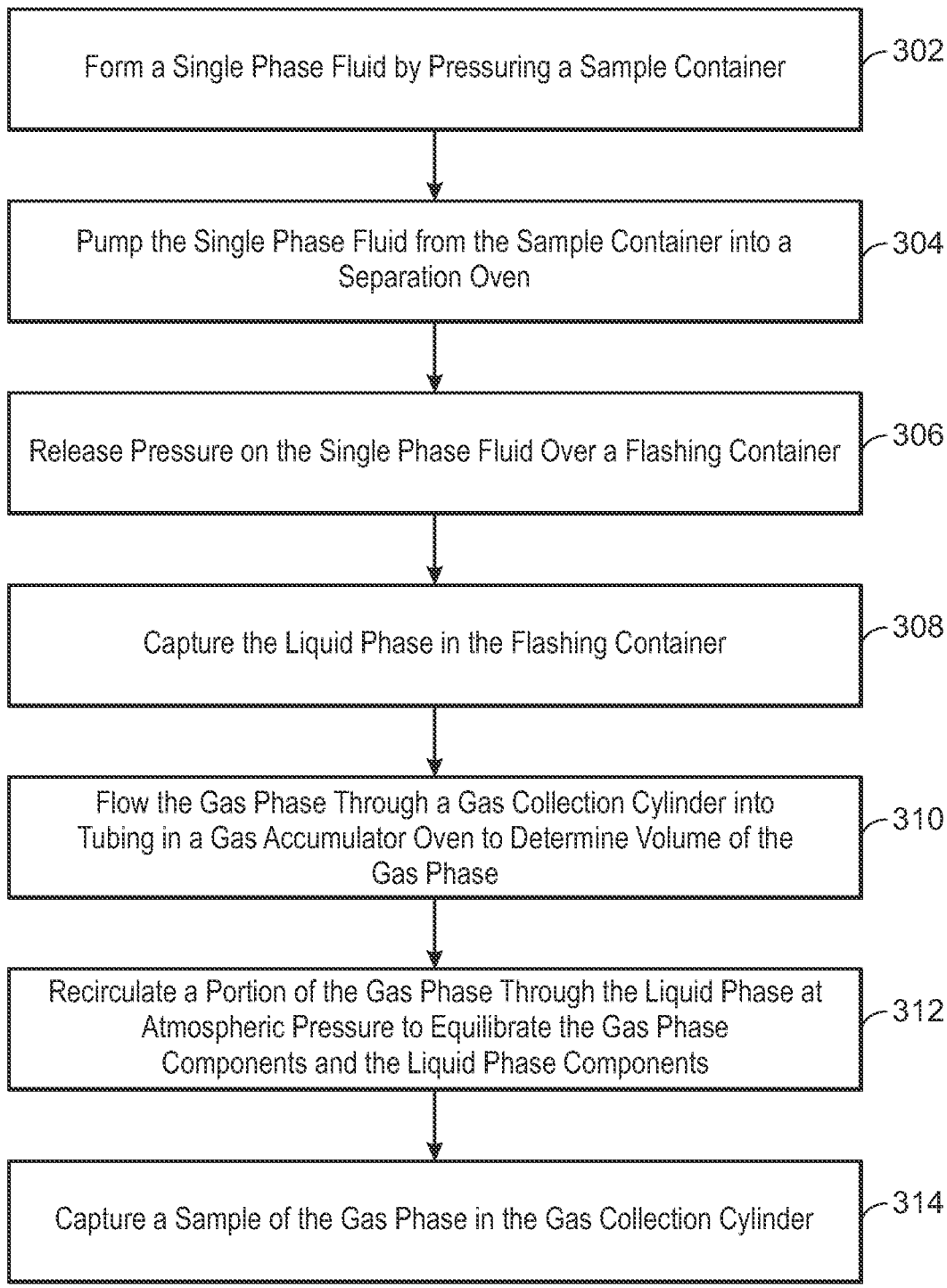
FIG. 3 is process flow diagram of a method for separating a reservoir fluid into components, using the direct-flash separator system.

FIG. 3 is process flow diagram of a method 300 for separating a reservoir fluid into components, using the direct-flash separator system. The method 300 begins at block 302 when a single-phase fluid is formed by pressurizing a sample container holding the reservoir fluid. At block 304, the single-phase fluid is pumped from the sample container into a separation oven. As used herein, pumped indicates that a pump provides pressure to a piston in the sample container, providing pressure to form the single-phase fluid in the sample container and then force the fluid from the sample container when a sample valve is opened.

At block 306, pressure is released on the single-phase fluid over a flashing container. The depressurizing allows the single-phase fluid to flashing into two separate phases, a liquid phase, and a gas phase. In some embodiments herein, the depressurizing is performed by a valve located on a line leading into the flashing container. Accordingly, the flashing occurs as the single-phase fluid passes through the valve. At block 308, the liquid phase is captured in the flashing container. The line is disposed near the bottom of the flashing container, to be below the liquid phase.

The flashing container is sealed at the top to force the gas phase out a second line. At block 310, the gas phase is flowed through a gas collection cylinder and into tubing in a gas accumulator oven. The capture of the gas phase allows the determination of the volume of the gas phase using a gas meter. At block 312, a portion of the gas phase is recirculated through the liquid phase atmospheric pressure to equilibrate the gas phase components and the liquid phase components. At block 314, a sample of the gas phase is collected in the gas collection cylinder. This is performed as described with respect to the examples, when a recirculation pump is turned off and valves are closed on each end of the gas collection cylinder.

Figure 4:
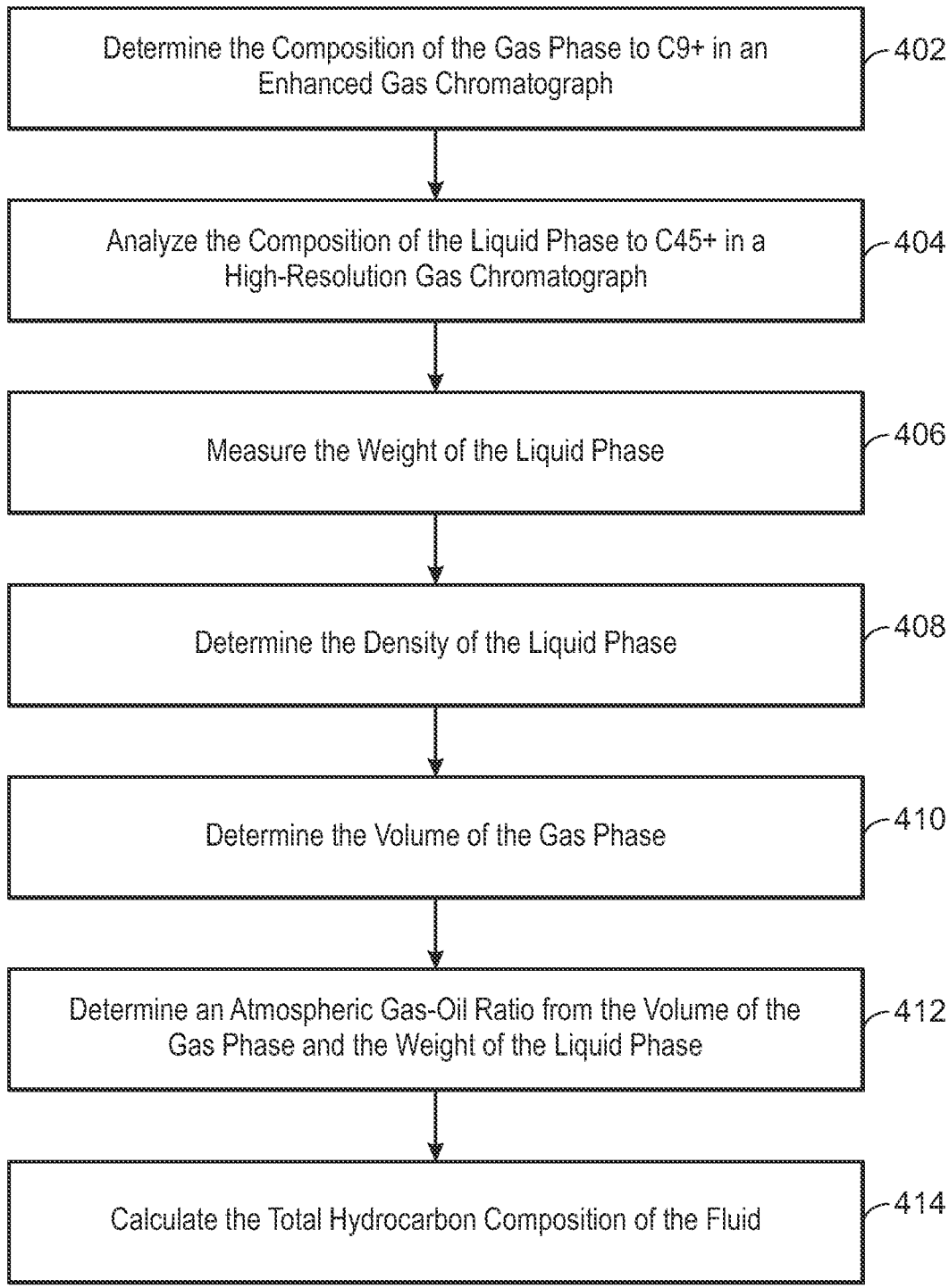
FIG. 4 is a process flow diagram of a method for using the liquid phase and gas phase samples collected from the direct-flash separator system to determine the hydrocarbon composition of a reservoir fluid.

FIG. 4 is a process flow diagram of a method 400 for using the liquid phase and gas phase samples collected from the direct-flash separator system to determine the hydrocarbon composition of a reservoir fluid. The method 400 begins at block 402 when the composition of the gas phase is determined to C9+ in an enhanced gas chromatograph. As used herein, an enhanced gas chromatograph includes at least two columns, one column using a total conductivity detector (TCD) to quantitate all gases including hydrocarbons and nonhydrocarbons, and another column using a flame ionization detector (FID) to quantitate the hydrocarbons. This is discussed further with respect to the examples.

At block 404, the composition of the liquid phase is determined to C45+ using a high-resolution gas chromatograph. This is discussed further with respect to the examples.

At block 406, the weight of the liquid phase is measured At block 408, the density of the liquid phase is determined. In some embodiments, this is performed using a densitometer, as described further with respect to the examples. In other embodiments, the density may be determined directly from the measured weight and volume of the liquid phase.

At block 410, the volume of the gas phase is determined. At block 412, an atmospheric gas-oil ratio (GOR) is determined. For example, this may be determined from the volume of the gas phase and the weight of the liquid phase.

At block 414, the total hydrocarbon composition of the reservoir fluid is determined. In various embodiments, this is performed by mathematically combining the amount of the gas phase, the amount of the liquid phase, the composition of the gas phase, the composition of the liquid phase, and the atmospheric gas-oil ratio (GOR). This is discussed further with respect to the examples.

EXAMPLES

A reservoir sample was flashed in the direct-flash separator system described with respect to FIG. 2. The operating procedure for conducting the direct flash using the direct-flash separator system are described in the following numbered paragraphs.

1. Pressurize the reservoir fluid in the sample cylinder (C1) to single-phase conditions using the positive displacement automatic pump. Heat the cylinder to 100° C., maintain the single-phase conditions for 5 hours.
2. Close all valves on the trek-flash separator system.
3. Weigh 100 cc glass flask (initial) and connect to tubing in the separation oven.
4. Open valves V1, V3, V4, V5, V6, V7, V9, V10, V13, and V15.
5. Connect a vacuum pump to valve V8 and evacuate the entire system.
6. Close valve V8 and check the system for leaks.
7. Close Valves V1, V3, V4, V5, V9, V10, and V13.
8. Connect low pressure (5 psi) Helium to V12 and open valve V12. Fill the entire system with Helium. Slowly open valve V13 until the gasometer piston just begins to move. Close valve V12. Record initial gas volume.
9. Open sample cylinder (C1) valve V19 and fill the tubing up to valve V1. Open valve V1 and fill the tubing up to valve V3.
10. Open valve V3 slowly to maintain sample single-phase conditions and low fluid flow rate downstream of valve V3. This will allow the fluid to flash across valve V3 into the glass flask forming gas and liquid phases.
11. Once flash is complete, close valves V3 and V15.
12. Record the final gas volume, pressure, and temperature from the gasometer.
13. Start the circulation pump (CP) and immediately open valves V4 and V5 to allow the gas phase to recirculate for 5 minutes through the liquid until equilibrium of gas and liquid phases are achieved.
14. Stop the circulation pump and close valves V4, V5, V6, and V7.
15. Disconnect the glass flask and weigh to obtain a final weight of the liquid phase.
16. Remove the gas cylinder C2 and determine the gas composition. Note: An additional gas sample is collected using C3 before disconnecting C2.
17. Determine composition, density, and molecular weight of flashed liquid as described herein.

Table 1 shows flash data recorded from the direct flash of a pressurized fluid sample using the direct flash separator recirculation system. A portion of the pressurized fluid is flashed from the single-phase fluid to atmospheric pressure at the specified temperature while maintaining single-phase conditions. During flashing, the single-phase fluid is separated into gas and liquid phases. The amounts of the phases are used to generate an atmospheric flash gas-oil ratio (GOR). The volume of flashed gas phase together with its pressure and temperature are measured using a digital gasometer. The weight of flashed liquid phase together with its molecular weight and density are also measured. The molecular weight of oil (liquid phase) is determined using Cryette A instrument. The density of oil (liquid phase) is measured using the Anton Paar DMA4500 digital densitometer. The composition of the gas phase is analyzed to C9+ using extended gas chromatography in terms of weight fractions. The liquid phase is analyzed to C45+ as described below (liquid phase composition to Pentatetracontanes plus) using high-resolution gas chromatograph technique in terms of weight fractions. The normalized gas and liquid weight fractions are mathematically recombined to the atmospheric flash gas-oil ratio. The recombined normalized weight fractions are then converted to mole fractions, by assigning molecular weights and densities using values published in the Engineering Data Book GPSA (1987), and the measured molecular weight and density, to obtain the total reservoir fluid composition to C45+.

The parameters measured from the direct flash of the single-phase fluid include, for the liquid phase, the weight, the molecular weight, and the density. For the gas phase, the parameters measured from the direct flash of the single-phase fluid include the volume, pressure, and temperature.

TABLE 1 flash data recorded from the direct flash of a pressurized fluid sample using the direct flash separator recirculation system
DIRECT FLASH SEPARATOR CALCULATION DATA SHEET

| Well Depth (ft) | Formation Formation P. (psia) | Type Formation T. (° F.) | Sampler No. Cylinder No. | Date Sampled Date Analysed |
|---|---|---|---|---|
| | | Gas Weight Data | | |
| | Pi(psi) | | 15.0 | |
| | Pf (psi) | | 15.0 | |
| | Vi(ml) | | 0.93 | |
| | Vf(ml) | | 2189.80 | |
| | T (° C.) | | 25.8 | |
| | | Residual Weight Data | | |
| | initial (g) | | 100.6623 | |
| | (+) Oil (g) | | 114.5561 | |
| | | Oil + C14 mixture | | |
| | C14 Added (g) | | 0.1070 | |
| | Oil (g) | | 1.0216 | |
| | Gas Specific Gravity | 1.3777 | Bottle | 15.2317 |
| | Density, grams/cc | 0.8506 | +Benzene | 24.2132 |
| | dFP reading (AVRG) | 439 | +Sample | 24.3725 |
| | Molecular Weight | 207 | | |

The remaining parameters used for the determination of the composition of the reservoir fluid are generated from gas chromatography analysis. These include the composition to C45+ for the liquid phase and the composition to C9+ for the gas phase.

High-Resolution GC analysis of the liquid phase for C2 to C45+

Crude oil is a mixture of hydrocarbons with wide range of molecular weights, densities, and boiling point fractions. Petroleum fluids exhibit a natural exponential decline of hydrocarbon components from C9-C11 (depending on type of fluid) to Cn+. The liquid phase is analyzed using high-resolution gas chromatography that utilizes a flame ionization detector (FID). It is based on the principle that the response from the GC-FID is proportional to the mass of hydrocarbon components. The determination of the hydrocarbon composition of the liquid phase of the flashed liquid up to C45+ is important to the determination of the total reservoir fluid composition. The various instrument parameters and conditions used in order to analyze hydrocarbon liquid to C45+ are provided in Table-2.

Prior to analyzing hydrocarbon liquid samples, an analysis blank or blank baseline, is run in order to subtract column bleed from the responses of the actual sample. As used herein, column bleed is an offset from baseline caused by the slow release of materials from previous analyses. To confirm the proper functioning of the gas chromatograph-flame ionization detector (GC-FID), a performance test is run using a standard reference n-paraffin mixture, for example, as characterized by ASTM D2887-19a (2019, 7.8.1.1 Note: 5), which provides a reference that includes known concentrations of hydrocarbons from C5 to C44. The relative response factor for each n-paraffin (relative to n-decane) is calculated in accordance with method ASTM D2887 (9.3.2 Eq. 2).

During gas chromatograph analyses, the hydrocarbon fractions beyond C44 are non-volatile material. These fractions will not elute from the column and cannot be determined by GC. The amount of nonvolatile material is determined by adding a known weight of an internal standard, such as normal tetradecane (nC14), to a known weight of the liquid phase, e.g., the flashed oil. The non-volatile material is quantified and added to C45 and is termed as C45 plus. Generally, the concentration of internal standard added to the liquid phase is in the range of 9 wt. %.

TABLE 2

High-resolution gas chromatography parameters for C2 to C45+ analysis

| | | |
|---|---|---|
| Instrument | Agilent 6890 N | |
| Carrier Gas | UHP Helium (99.999%) | |
| Column | Ultra-Alloy Capillary Column | |
| | Length, meters | 30 |
| | I.D., mm | 0.25 |
| | Film Thickness, μm | 0.25 |
| | Carrier Gas Flow Rate, ml/min | 5 |
| Oven | Initial Temperature | 30° C. |
| | Initial Time | 3 min |
| | Rate | 10° C./min |
| | Final Temperature | 350° C. |
| | Run Time | 65 min |
| Front Inlet (Split/Splitless) | Mode | Split |
| | Temperature | 300° C. |
| | Split Ratio | 15:1' |
| | Split Flow | 25 ml/min |
| Front Detector (Flame Ionization Detector) | Temperature | 370° C. |
| | Hydrogen Flow | 30 ml/min |
| | Air Flow | 300 ml/min |
| | Makeup Flow | 45 ml/min |
| | Makeup Gas Type | Helium |

The mixture of the liquid phase and the internal standard is diluted with carbon disulfide in a proportion of 90:10 liquid to $CS_2$. The dilution lowers the viscosity of the sample and decreases the amount of hydrocarbons, which helps to prevent overloading of the FID, as the FID does not respond to $CS_2$. A known amount of the liquid mixture, such as 0.20 microliters (μL), is then injected at the front end of the GC split injector. A computer equipped with data acquisition and processing software, termed a "Chemstation" for the model of GC used, converts the FID signals to peak areas for each hydrocarbon component.

Figure 5:
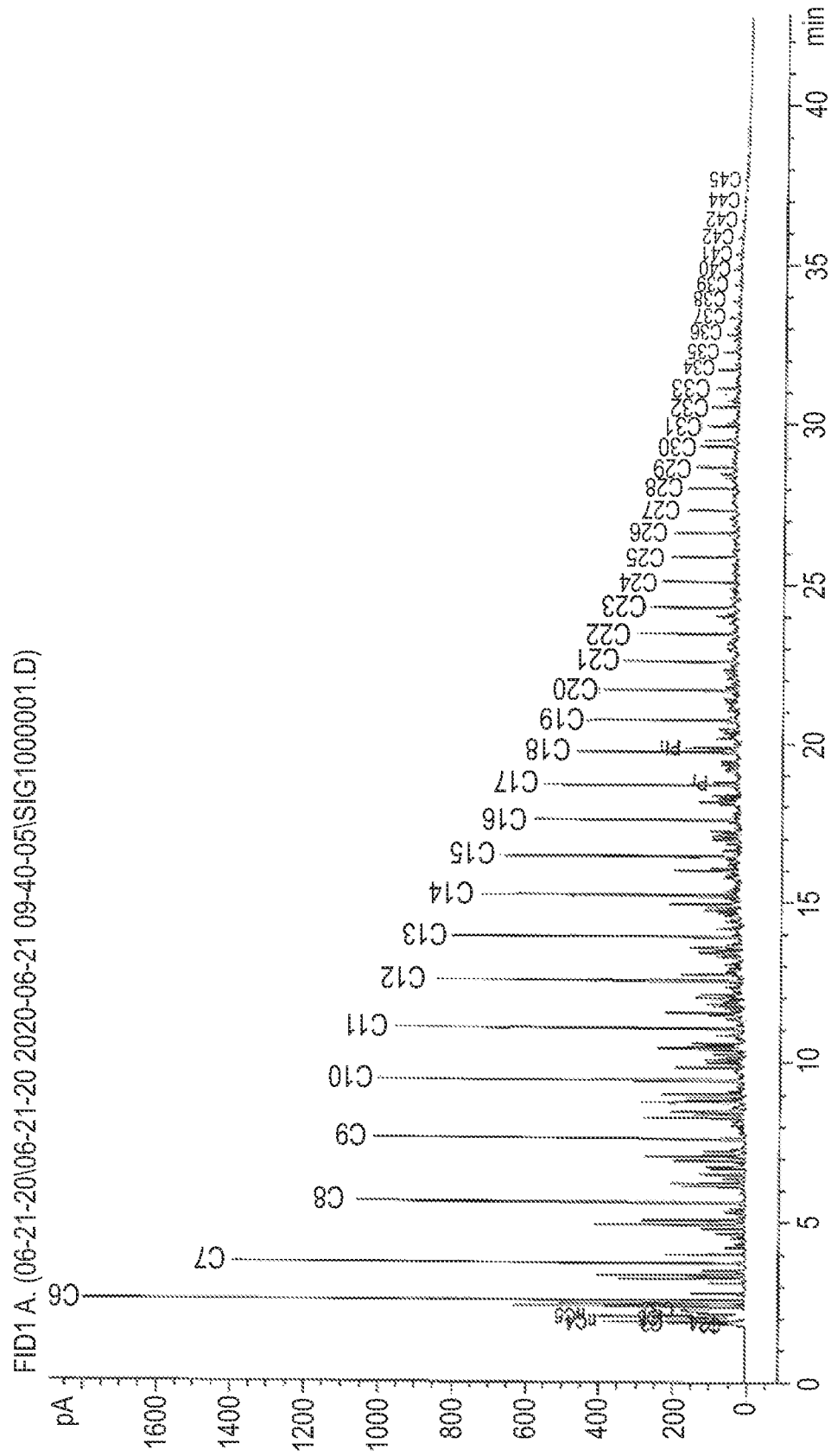
FIG. 5 is a high-resolution liquid chromatogram of the liquid phase sample of a reservoir fluid showing peaks from C2 to C45+, collected for the sample recorded in Table 1.

FIG. 5 is a high-resolution liquid chromatogram 500 of the liquid phase sample of a reservoir fluid showing peaks from C2 to C45+, collected for the sample recorded in Table 1. The composition for the liquid phase are shown in Table 3, and are expressed in terms of mole percentage and weight percentage, in addition to plus fraction properties for C7+, C10+, C12+, C36+, and C45+ fractions.

TABLE 3A

Flashed liquid composition results

| Comp. | MW | Density | Original Peak Area Counts B | Adjusted Peak Area Counts C | Assembled Peak Area Counts G | Norm. Liquid Wt. % | Liquid Moles | Norm. Liquid Mole % | Liquid Volume cc |
|---|---|---|---|---|---|---|---|---|---|
| N2 | 28.01 | 0.8086 | 0 | 0 | 0 | 0.00 | 0.0000 | 0.00 | 0.0000 |
| CO2 | 44.01 | 0.8172 | 0 | 0 | 0 | 0.00 | 0.0000 | 0.00 | 0.0000 |
| H2S | 34.08 | 0.8006 | 0 | 0 | 0 | 0.00 | 0.0000 | 0.00 | 0.0000 |
| C1 | 16.04 | 0.2997 | 0 | 0 | 0 | 0.00 | 0.0000 | 0.00 | 0.0000 |
| C2 | 30.07 | 0.3562 | 35 | 35 | 35 | 0.04 | 0.0012 | 0.24 | 0.0989 |
| C3 | 44.10 | 0.5070 | 186 | 186 | 186 | 0.19 | 0.0042 | 0.88 | 0.3692 |
| iC4 | 58.12 | 0.5629 | 469 | 469 | 469 | 0.47 | 0.0081 | 1.68 | 0.8386 |
| nC4 | 58.12 | 0.5840 | 97 | 97 | 97 | 0.10 | 0.0017 | 0.35 | 0.1672 |
| iC5 | 72.15 | 0.6244 | 807 | 807 | 807 | 0.81 | 0.0113 | 2.33 | 1.3008 |
| nC5 | 72.15 | 0.6311 | 451 | 451 | 451 | 0.45 | 0.0063 | 1.30 | 0.7192 |
| C6 | 84 | 0.6850 | 2099 | 2099 | 2099 | 2.11 | 0.0251 | 5.20 | 3.0840 |
| C7 | 96 | 0.7220 | 3618 | 3618 | 3618 | 3.64 | 0.0379 | 7.85 | 5.0435 |
| C8 | 107 | 0.7450 | 4918 | 4918 | 4918 | 4.95 | 0.0463 | 9.57 | 6.6440 |
| C9 | 121 | 0.7640 | 4742 | 4742 | 4742 | 4.77 | 0.0394 | 8.16 | 6.2469 |
| C10 | 134 | 0.7780 | 4858 | 4858 | 4858 | 4.89 | 0.0365 | 7.55 | 6.2846 |
| C11 | 147 | 0.7890 | 4314 | 4314 | 4314 | 4.34 | 0.0295 | 6.11 | 5.5030 |
| C12 | 161 | 0.8000 | 3787 | 3787 | 3787 | 3.81 | 0.0237 | 4.90 | 4.7643 |
| C13 | 175 | 0.8110 | 3715 | 3715 | 3715 | 3.74 | 0.0214 | 4.42 | 4.6104 |
| C14 | 190 | 0.8220 | 13929 | 3523 | 3523 | 3.55 | 0.0187 | 3.86 | 4.3130 |
| C15 | 206 | 0.8320 | 3330 | 3330 | 3330 | 3.35 | 0.0163 | 3.37 | 4.0283 |
| C16 | 222 | 0.8390 | 3025 | 3025 | 3025 | 3.04 | 0.0137 | 2.84 | 3.6288 |
| C17 | 237 | 0.8470 | 2839 | 2839 | 2839 | 2.86 | 0.0121 | 2.49 | 3.3735 |
| C18 | 251 | 0.8520 | 2689 | 2689 | 2689 | 2.71 | 0.0108 | 2.23 | 3.1765 |
| C19 | 263 | 0.8570 | 2802 | 2802 | 2802 | 2.82 | 0.0107 | 2.22 | 3.2907 |
| C20 | 275 | 0.8620 | 2450 | 2450 | 2450 | 2.47 | 0.0090 | 1.85 | 2.8606 |
| C21 | 291 | 0.8670 | 2342 | 2342 | 2342 | 2.36 | 0.0081 | 1.68 | 2.7187 |
| C22 | 305 | 0.8720 | 2145 | 2145 | 2145 | 2.16 | 0.0071 | 1.46 | 2.4758 |
| C23 | 318 | 0.8770 | 1980 | 1980 | 1980 | 1.99 | 0.0063 | 1.30 | 2.2723 |
| C24 | 331 | 0.8810 | 1848 | 1848 | 1848 | 1.86 | 0.0056 | 1.16 | 2.1112 |
| C25 | 345 | 0.8850 | 1835 | 1835 | 1835 | 1.85 | 0.0054 | 1.11 | 2.0868 |
| C26 | 359 | 0.8890 | 1802 | 1802 | 1802 | 1.81 | 0.0051 | 1.05 | 2.0401 |
| C27 | 374 | 0.8930 | 1811 | 1811 | 1811 | 1.82 | 0.0049 | 1.01 | 2.0411 |
| C28 | 388 | 0.8960 | 1686 | 1686 | 1686 | 1.70 | 0.0044 | 0.90 | 1.8939 |
| C29 | 402 | 0.8990 | 1732 | 1732 | 1732 | 1.74 | 0.0043 | 0.90 | 1.9390 |
| C30 | 416 | 0.9020 | 1691 | 1691 | 1691 | 1.70 | 0.0041 | 0.85 | 1.8868 |
| C31 | 430 | 0.9060 | 1603 | 1603 | 1603 | 1.61 | 0.0038 | 0.78 | 1.7808 |
| C32 | 444 | 0.9090 | 1390 | 1390 | 1390 | 1.40 | 0.0032 | 0.65 | 1.5390 |
| C33 | 458 | 0.9120 | 1298 | 1298 | 1298 | 1.31 | 0.0029 | 0.59 | 1.4324 |
| C34 | 472 | 0.9140 | 1342 | 1342 | 1342 | 1.35 | 0.0029 | 0.59 | 1.4778 |
| C35 | 486 | 0.9170 | 1058 | 1058 | 1058 | 1.06 | 0.0022 | 0.45 | 1.1612 |
| C36 | 500 | 0.9190 | 1105 | 1105 | 1105 | 1.11 | 0.0022 | 0.46 | 1.2102 |
| C37 | 514 | 0.9220 | 914 | 914 | 914 | 0.92 | 0.0018 | 0.37 | 0.9977 |
| C38 | 528 | 0.9240 | 912 | 912 | 912 | 0.92 | 0.0017 | 0.36 | 0.9934 |
| C39 | 542 | 0.9260 | 796 | 796 | 796 | 0.80 | 0.0015 | 0.31 | 0.8652 |
| C40 | 556 | 0.9280 | 753 | 753 | 753 | 0.76 | 0.0014 | 0.28 | 0.8167 |
| C41 | 570 | 0.9300 | 676 | 676 | 676 | 0.68 | 0.0012 | 0.25 | 0.7316 |
| C42 | 584 | 0.9310 | 626 | 626 | 626 | 0.63 | 0.0011 | 0.22 | 0.6767 |
| C43 | 598 | 0.9330 | 498 | 498 | 498 | 0.50 | 0.0008 | 0.17 | 0.5372 |
| C44 | 612 | 0.9350 | 450 | 450 | 450 | 0.45 | 0.0007 | 0.15 | 0.4844 |
| C45+ | 719 | 1.1215 | 1501 | 1501 | 12311 | 12.39 | 0.0172 | 3.57 | 11.0481 |
| Total | | | 98,954 | 88,548 | 99,358 | 100.00 | 0.4834 | 100.00 | 117.5641 |

TABLE 3B

Flashed liquid composition results- Plus Fraction Properties.

| Component | Mole % | Grams | Moles | Volume | Mole Wt | Density |
|---|---|---|---|---|---|---|
| C7+ | 88.0196 | 0.9583 | 0.4255 | 110.9861 | 225 | 0.8634 |
| C10+ | 62.4449 | 0.7007 | 0.2846 | 93.0517 | 246 | 0.7531 |
| C12+ | 48.7872 | 0.7323 | 0.2358 | 81.2641 | 311 | 0.9012 |
| C36+ | 6.1408 | 0.1916 | 0.0297 | 18.3611 | 646 | 1.0437 |
| C45+ | 3.5666 | 0.1239 | 0.0172 | 11.0481 | 719 | 1.1215 |

The high-resolution chromatography data may be used to calculate the hydrocarbon composition of the liquid phase using the internal standard ($nC_{14}$). The calculation is performed as described below. The amount of internal standard added is calculated using equation 1.

$$\text{Original Internal Standard } C14\ \% = \frac{\text{Weight } C14}{\text{weight } C14 + \text{Weight oil}} \times 100 = A \quad (1)$$

The chromatogram is processed (2) using Agilent gas chromatograph Chemstation software. The software converts peak areas to peak area counts. The area count of each hydrocarbon component indicates the weight of that component in the liquid mixture.

$$\text{Quantify chromatographic data } (C2 \text{ to } C45+) = B \quad (2)$$

It is assumed that there is an exponential decline of hydrocarbon components from C10 or C11 to C45. Based on this assumption, the C14 area count is calculated as the average of C13 & C15 area counts (equation 3).

$$\text{Adjusted Peak Area } C14 = \text{Average}(C13, C15) = C \quad (3)$$

The amount of internal standard area counts recovered from the column is obtained by subtracting total adjusted peak area from the total original peak area (equation 4).

$$\text{Internal Standard Area } C14 \text{ Recovered} = \Sigma(B) - \Sigma(C) = D \quad (4)$$

However, the true area counts recovered from the column is calculated using equation 5.

$$\text{True Area Recovered} = \frac{D \times 100}{A} = E \quad (5)$$

Therefore, the amount of nonvolatile material not eluted from the column is calculated by subtracting true area recovered from the total original area count (equation 6).

$$\text{Nonvolatile Material Area} = E - B = F \quad (6)$$

The new C45 plus area count is now calculated by adding the nonvolatile material area not recovered from the column to the original C45 peak area count (equation 7).

$$\text{New } C45 \text{ plus Area} = \text{Original } C45 \text{ plus Area} + F(\text{Nonvolatile Material Area}) \quad (7)$$

Subsequently, all component peak area counts are assembled (equation 8).

$$\text{Assembled Peak Areas} = G \quad (8)$$

The peak area count of each component assembled is normalized to give the weight percent distribution (equation 9)

$$\text{Normalised Liquid Weight Component Distribution \%} = \frac{\text{Hydrocarbon Component Each Peak Area (Step 8)}}{\sum G(\text{total assembled peak area counts})} \quad (9)$$

Calculation of C45+ properties (molecular weight and density) and plus fraction properties.

The molecular weights and densities are assigned from C2 to C44 using values published in the Engineering Data Book GPSA (1987).

Based on 100 grams of liquid, the relationship between moles and molecular weight of each component can be expressed as equation 10.

$$\text{Moles Each Component } (C2 \text{ to } C44) = \frac{\text{Liquid Weight\% of Each Component}}{\text{Molecular Weight of Each Component}} \quad (10)$$

Based on 100 grams of liquid, the C45 plus moles is calculated (equation 11).

$$\text{Moles } C45 \text{ plus} = \frac{100}{\text{Molecular Weight of stock tank oil}} - \sum \text{Moles each Component } (C2 \text{ to } C44) \quad (11)$$

Subsequently, the total moles of liquid is calculated (equation 12).

$$\text{Total Liquid Moles} = \sum \begin{bmatrix} \text{Moles Each Component } (C2 - C44) + \\ \text{Moles } C45 \text{ plus} \end{bmatrix} \quad (12)$$

Therefore, the C45 plus molecular weight is calculated using equation 13.

$$\text{Molecular Weight } C45 \text{ plus} = \frac{C45 + \text{liquid Weight}}{\text{Moles } C45 \text{ plus (step3)}} \quad (13)$$

The normalized mole distribution is calculated using equation 14.

$$\text{Normalised Liquid Mole Component Distribution \%} = \frac{\text{Mole Each Component (Step 2, Step 3)}}{\text{Total } Lqiuid \text{ Moles (Step 4)}} \quad (14)$$

Based on 100 grams of liquid, the relationship between volume and density can be expressed as equation 15.

$$\text{Volume Each Component } (C2 \text{ to } C44) = \frac{\text{Liquid Weight of Each Component}}{\text{Density of Each Component}} \quad (15)$$

Based on 100 grams of liquid, the C45 plus volume is calculated using equation 16.

$$\text{Volume } C45 \text{ plus} = \frac{100}{\text{Density of stock tank oil}} - \sum \text{Volume Components } (C2 \text{ to } C44) \quad (16)$$

Subsequently, the total volume of liquid is calculated using equation 17.

$$\text{Total Liquid Volume} = \sum \left[ \text{Volume Each Component } (C2 - C44) + \text{Volume } C45 \text{ plus} \right] \quad (17)$$

Therefore, the C45 plus density is calculated using equation 18.

$$\text{Density } C45 \text{ plus} = \frac{C45 \text{ plus total Liquid Weight}}{\text{Volume } C45 \text{ plus (step 8)}} \quad (18)$$

Using the mole fractions, weight fractions & volume fractions of the components, the plus fraction properties (molecular & density) is calculated using equations 19 & 20 where n=heptanes, decanes, dodecanes, hexatriacontanes, and pentatetracontanes.

$$\sum C_{n+} \text{ Molecular Weight} = \frac{\sum C_{n+} \text{ weight}}{\sum C_{n+} \text{ moles}} = \text{plus fraction molecular weight} \quad (19)$$

$$\sum C_{n+} \text{ Density} = \frac{\sum C_{n+} \text{ weight}}{\sum C_{n+} \text{ volume}} = \text{plus fraction density} \quad (20)$$

Determination of the composition of the gas phase by extended GC.

The flashed gas composition is determined by utilizing an extended natural gas analyzer GC that allows the detection of non-hydrocarbon components (O2, N2, CO2, and H2S) and hydrocarbon components from C1 through C9+ in a single injection. The various instrument parameters and conditions to analyze flashed gas are provided in Table 3.

The gas phase sample is introduced via an S/SL inlet and a 10-port dual sample loop valve. The sample entry system is evacuated to avoid air contamination in gas sample. A single charge allows the gas to simultaneously flow directly into column 1 (HP-Plot Q) and column 2 (HP-Mole Sieve) in a single time injection. The GC comprises three channel configurations.

The front and back channels are connected to column 1 (HP-Plot Q). The effluent from this column are split between a back thermoconductivity detector (TCD) which is connected in series to a front FID. The elution pattern for the back TCD is air, $CO_2$, $H_2S$, $C_1$, $CO_2$, $C_2$, $H_2S$, $C_3$, $iC_4$, $nC_4$, $iC_5$, and $nC_5$. The elution pattern for the front FID is $C_1$, $C_2$, $C_3$, $iC_4$, $nC_4$, $iC_5$, $nC_5$, $C_6$, $C_7$, $C_8$, and $C_9+$.

The aux side channel is connected to column 2 (HP-Mole Sieve) and effluents from this column flows into aux side TCD. The elution pattern for the aux side TCD is $O_2$, $N_2$, and $C_1$.

The signals from these three detectors (front, back and aux side) are independently collected and the results combined using a computer equipped with data acquisition and processing system. In this example, the data acquisition and processing system is a ChemStation, from Hewlett Packard Cor. Prior to analyzing gas samples, the gas chromatograph is calibrated using reference gas standard. The instrument setup and the calibration procedures match the requirements of ASTM D1945-14 (reapproved 2019), § 7.1; § 8.3.1; § 9.

TABLE 4

| Extended GC parameters | | |
|---|---|---|
| Instrument | Agilent 7890 B | |
| Carrier Gas | UHP Helium (99.999%) | |
| Oven | Initial Temperature | 60° C. |
| | Initial Time | 2 min |
| | Rate | 25° C./min |
| | Final Temperature | 250°/C. |
| | Run Time | 15 min |
| Front Inlet | Mode | Split |
| | Temperature | 250° C. |
| | Split Ratio | 3:1' |
| | Split Flow | 12 ml/min |
| Back Inlet | Mode | Split |
| | Temperature | 250° C. |
| | Split Ratio | 3:1' |
| | Split Flow | 120 ml/min |
| Column 1 | HP-PLOT Q | |
| | Length, meters | 30 |
| | I.D., mm | 0.53 |
| | Film Thickness, μm | 40 |
| | In | Front SS Inlet He |
| | Out | 60° C. |
| | Pressure | 5.6677 psi |
| | Flow | 4 ml/min |
| | Hole Up Time | 1.2844 min |
| Column 2 | HP-Molesieve | |
| | Length, meters | 30 |
| | I.D., mm | 0.53 |
| | Film Thickness, μm | 25 |
| | In | Bach SS Inlet He |
| | Out | 60° C. |
| | Pressure | 27.148 psi |
| | Flow | 40 ml/min |
| | Hole Up Time | 0.2516 min |
| Front Detector (Flame Ionization Detector) | Temperature | 250° C. |
| | Hydrogen Flow | 45 ml/min |
| | Air Flow | 450 ml/min |
| | Makeup Flow | 10 ml/min |
| | Makeup Gas Type | Helium |
| Back Detector (Thermal Conductivity Detector) | Temperature | 250° C. |
| | Reference Flow | 25 ml/min |
| | Makeup Flow | 2 ml/min |
| | Makeup Gas Type | Helium |
| Aux Side Detector (Thermal Conductivity Detector) | Temperature | 250° C. |
| | Reference Flow | 25 ml/min |
| | Makeup Flow | 2 ml/min |
| | Makeup Gas Type | Helium |

TABLE 5

| Composition of gas phase | | | |
|---|---|---|---|
| Component | Mole % | Weight % | Liquid Vol % |
| Nitrogen | 0.42 | 0.30 | 0.19 |
| Carbon Dioxide | 3.64 | 4.01 | 2.45 |

TABLE 5-continued

Composition of gas phase

| Component | Mole % | Weight % | Liquid Vol % |
|---|---|---|---|
| Hydrogen Sulfide | 10.69 | 9.13 | 5.82 |
| Methane | 17.53 | 7.05 | 11.84 |
| Ethane | 23.02 | 17.35 | 24.54 |
| Propane | 22.05 | 24.36 | 24.20 |
| i-Butane | 2.53 | 3.68 | 3.30 |
| n-Butane | 9.98 | 14.54 | 12.54 |
| i-Pentane | 2.43 | 4.40 | 3.55 |
| n-Pentane | 4.22 | 7.63 | 6.10 |
| Hexanes | 2.85 | 6.00 | 4.39 |
| Heptanes | 0.57 | 1.36 | 0.95 |
| Octanes | 0.07 | 0.19 | 0.13 |
| Nonanes | 0.00 | 0.00 | 0.00 |
| Decanes | 0.00 | 0.00 | 0.00 |
| Total | 100.00 | 100.00 | 100.00 |
| Specific Gravity (Air = 0.0) | 1.3777 | | |
| Gross Heating Value | 2,053 BTU/SCF | | |

Figure 6:
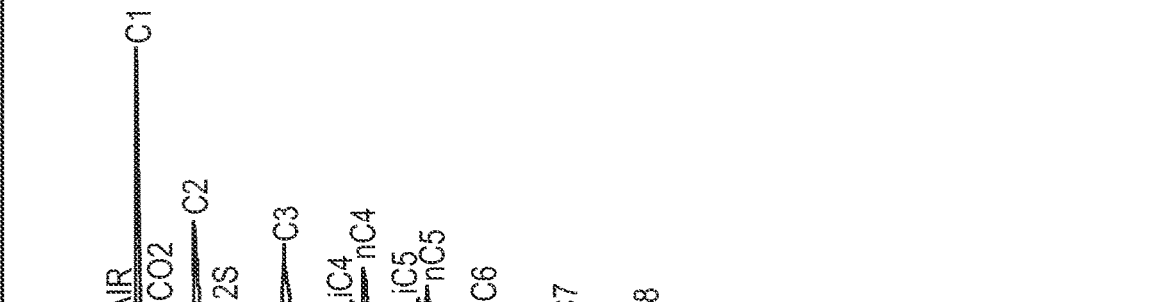
FIG. 6 are the chromatograms from the three detectors of the gas analyzer for the configuration set-up described in Table 4.
Figure 6:
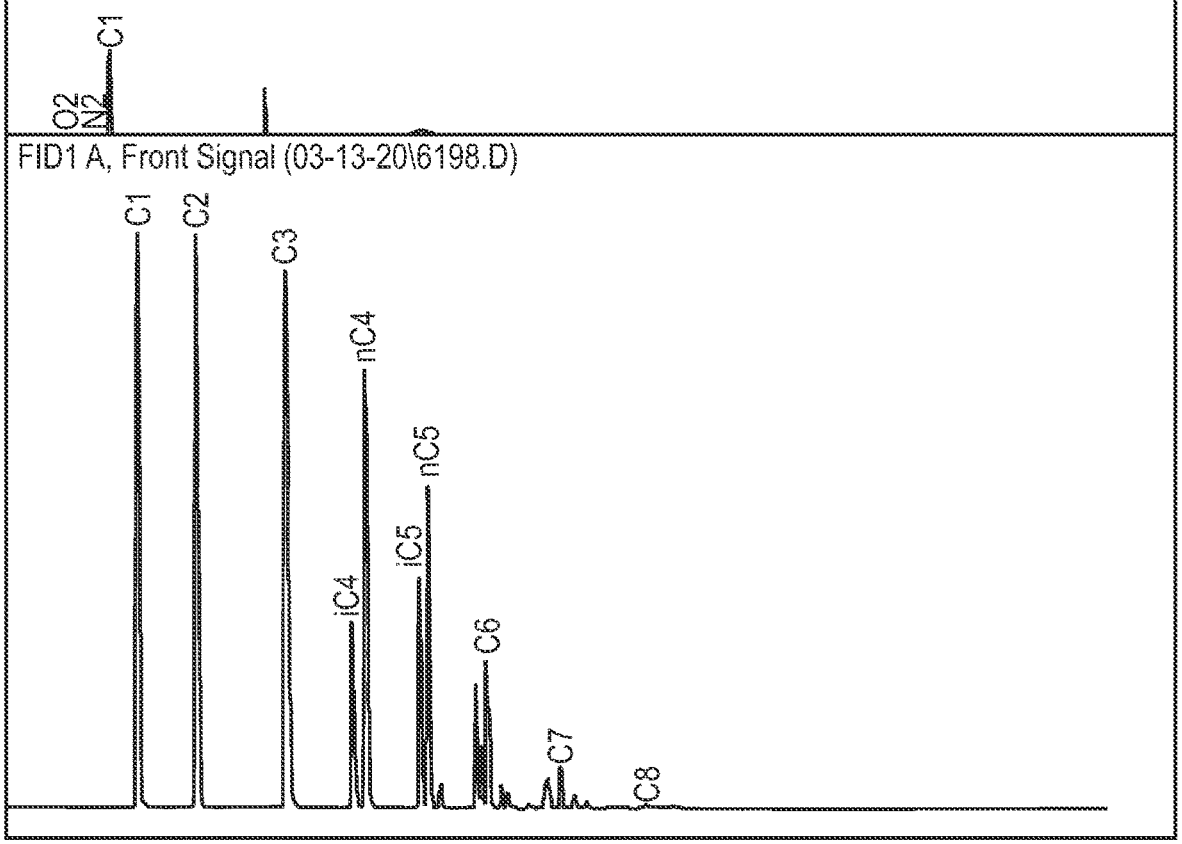

FIG. 6 are the chromatograms 600 from the three detectors of the gas analyzer for the configuration set-up described in Table 4. Table 5 shows the results of the analyses for the composition of the gas phase composition in terms of mole percentage, weight percentage, specific gravity, and molecular weight.

Total Reservoir Fluid Composition

The total reservoir fluid composition may then calculated from the results obtained using the techniques discussed above. To begin, the atmospheric gas-oil ratio generated from the direct flash technique is converted to weight-weight ratio. The weight of oil is obtained by subtracting the final glass weight from the initial glass weight (Table 1). The weight of gas is calculated by inputting volume of gas, its pressure and temperature and molecular weight of gas (Table 1) into gas law equation. The flashed product compositions are then combined with the weights of gas and liquid to obtain the total fluid composition in terms of weight percentage as described in Eqn. 21.

Weight % of each hydrocarbon component=(weight of gas×weight % of each gas component from gas composition)+(weight of liquid×weight % of each liquid component from liquid composition) (21)

The weight percentage is then converted to mole percentage using the molecular weights of each hydrocarbon component from C2 to C44 assigned from values published in the Engineering Data Book GPSA (1987). The mole percentage of C45+ is calculated using the molecular weight and density of C45+ calculated from flashed liquid composition process, and plus fraction properties described above.

The volume of C45+ is calculated using the density of the C45 liquid fraction calculated from flashed liquid composition process described above. The plus fraction properties are calculated using equations 11 and 12 described in the calculation of flashed liquid to C45+ properties (molecular weight and density). The total reservoir fluid composition is shown in Table 6 in mole percentage and weight percentage and plus fraction properties (C7+, C10+, C12+, C36+, C45+). The analyses were performed using 13.8938 g Oil, and 2.7960 g gas.

TABLE 6A

Total reservoir fluid composition to C45+

| Cmp. | MW | Density | Liquid Weight % | Gas Weight % | Liquid grams | Gas grams | Total grams | Norm. Total Weight % | Moles | Norm. Total Mole % | Vol. cc |
|---|---|---|---|---|---|---|---|---|---|---|---|
| N2 | 28.01 | 0.8086 | 0.00 | 0.30 | 0.0000 | 0.0084 | 0.0084 | 0.05 | 0.00179 | 0.22 | 0.0622 |
| CO2 | 44.01 | 0.8172 | 0.00 | 4.01 | 0.0000 | 0.1121 | 0.1121 | 0.67 | 0.01526 | 1.86 | 0.8221 |
| H2S | 34.08 | 0.8006 | 0.00 | 9.13 | 0.0000 | 0.2553 | 0.2553 | 1.53 | 0.04488 | 5.46 | 1.9104 |
| C1 | 16.04 | 0.2997 | 0.00 | 7.05 | 0.0000 | 0.1971 | 0.1971 | 1.18 | 0.07362 | 8.95 | 3.9409 |
| C2 | 30.07 | 0.3562 | 0.04 | 17.35 | 0.0049 | 0.4851 | 0.4900 | 2.94 | 0.09764 | 11.87 | 8.2425 |
| C3 | 44.10 | 0.5070 | 0.19 | 24.36 | 0.0260 | 0.6811 | 0.7071 | 4.24 | 0.09608 | 11.68 | 8.3567 |
| iC4 | 58.12 | 0.5629 | 0.47 | 3.68 | 0.0656 | 0.1029 | 0.1685 | 1.01 | 0.01737 | 2.11 | 1.7933 |
| nC4 | 58.12 | 0.5840 | 0.10 | 14.54 | 0.0136 | 0.4065 | 0.4201 | 2.52 | 0.04331 | 5.27 | 4.3102 |
| iC5 | 72.15 | 0.6244 | 0.81 | 4.40 | 0.1128 | 0.1230 | 0.2359 | 1.41 | 0.01959 | 2.38 | 2.2634 |
| nC5 | 72.15 | 0.6311 | 0.45 | 7.63 | 0.0631 | 0.2133 | 0.2764 | 1.66 | 0.02295 | 2.79 | 2.6242 |
| C6 | 84 | 0.6850 | 2.11 | 6.00 | 0.2935 | 0.1678 | 0.4613 | 2.76 | 0.03290 | 4.00 | 4.0348 |
| C7 | 96 | 0.7220 | 3.64 | 1.36 | 0.5059 | 0.0380 | 0.5440 | 3.26 | 0.03395 | 4.13 | 4.5141 |
| C8 | 107 | 0.7450 | 4.95 | 0.19 | 0.6877 | 0.0053 | 0.6930 | 4.15 | 0.03881 | 4.72 | 5.5737 |
| C9 | 121 | 0.7640 | 4.77 | 0.00 | 0.6631 | 0.0000 | 0.6631 | 3.97 | 0.03284 | 3.99 | 5.2004 |
| C10 | 134 | 0.7780 | 4.89 | 0.00 | 0.6793 | 0.0000 | 0.6793 | 4.07 | 0.03038 | 3.69 | 5.2317 |
| C11 | 147 | 0.7890 | 4.34 | 0.00 | 0.6033 | 0.0000 | 0.6033 | 3.61 | 0.02459 | 2.99 | 4.5811 |
| C12 | 161 | 0.8000 | 3.81 | 0.00 | 0.5296 | 0.0000 | 0.5296 | 3.17 | 0.01971 | 2.40 | 3.9662 |
| C13 | 175 | 0.8110 | 3.74 | 0.00 | 0.5195 | 0.0000 | 0.5195 | 3.11 | 0.01779 | 2.16 | 3.8380 |
| C14 | 190 | 0.8220 | 3.55 | 0.00 | 0.4926 | 0.0000 | 0.4926 | 2.95 | 0.01553 | 1.89 | 3.5904 |
| C15 | 206 | 0.8320 | 3.35 | 0.00 | 0.4657 | 0.0000 | 0.4657 | 2.79 | 0.01354 | 1.65 | 3.3534 |
| C16 | 222 | 0.8390 | 3.04 | 0.00 | 0.4230 | 0.0000 | 0.4230 | 2.53 | 0.01142 | 1.39 | 3.0209 |
| C17 | 237 | 0.8470 | 2.86 | 0.00 | 0.3970 | 0.0000 | 0.3970 | 2.38 | 0.01004 | 1.22 | 2.8083 |
| C18 | 251 | 0.8520 | 2.71 | 0.00 | 0.3760 | 0.0000 | 0.3760 | 2.25 | 0.00898 | 1.09 | 2.6443 |
| C19 | 263 | 0.8570 | 2.82 | 0.00 | 0.3918 | 0.0000 | 0.3918 | 2.35 | 0.00893 | 1.09 | 2.7394 |
| C20 | 275 | 0.8620 | 2.47 | 0.00 | 0.3426 | 0.0000 | 0.3426 | 2.05 | 0.00746 | 0.91 | 2.3814 |
| C21 | 291 | 0.8670 | 2.36 | 0.00 | 0.3275 | 0.0000 | 0.3275 | 1.96 | 0.00674 | 0.82 | 2.2633 |
| C22 | 305 | 0.8720 | 2.16 | 0.00 | 0.2999 | 0.0000 | 0.2999 | 1.80 | 0.00589 | 0.72 | 2.0610 |
| C23 | 318 | 0.8770 | 1.99 | 0.00 | 0.2769 | 0.0000 | 0.2769 | 1.66 | 0.00522 | 0.63 | 1.8916 |
| C24 | 331 | 0.8810 | 1.86 | 0.00 | 0.2584 | 0.0000 | 0.2584 | 1.55 | 0.00468 | 0.57 | 1.7575 |
| C25 | 345 | 0.8850 | 1.85 | 0.00 | 0.2566 | 0.0000 | 0.2566 | 1.54 | 0.00446 | 0.54 | 1.7372 |
| C26 | 359 | 0.8890 | 1.81 | 0.00 | 0.2520 | 0.0000 | 0.2520 | 1.51 | 0.00421 | 0.51 | 1.6983 |
| C27 | 374 | 0.8930 | 1.82 | 0.00 | 0.2532 | 0.0000 | 0.2532 | 1.52 | 0.00406 | 0.49 | 1.6992 |
| C28 | 388 | 0.8960 | 1.70 | 0.00 | 0.2358 | 0.0000 | 0.2358 | 1.41 | 0.00364 | 0.44 | 1.5766 |

TABLE 6A-continued

Total reservoir fluid composition to C45+

| Cmp. | MW | Density | Liquid Weight % | Gas Weight % | Liquid grams | Gas grams | Total grams | Norm. Total Weight % | Moles | Norm. Total Mole % | Vol. cc |
|---|---|---|---|---|---|---|---|---|---|---|---|
| C29 | 402 | 0.8990 | 1.74 | 0.00 | 0.2422 | 0.0000 | 0.2422 | 1.45 | 0.00361 | 0.44 | 1.6142 |
| C30 | 416 | 0.9020 | 1.70 | 0.00 | 0.2365 | 0.0000 | 0.2365 | 1.42 | 0.00341 | 0.41 | 1.5707 |
| C31 | 430 | 0.9060 | 1.61 | 0.00 | 0.2242 | 0.0000 | 0.2242 | 1.34 | 0.00312 | 0.38 | 1.4824 |
| C32 | 444 | 0.9090 | 1.40 | 0.00 | 0.1944 | 0.0000 | 0.1944 | 1.16 | 0.00262 | 0.32 | 1.2812 |
| C33 | 458 | 0.9120 | 1.31 | 0.00 | 0.1815 | 0.0000 | 0.1815 | 1.09 | 0.00237 | 0.29 | 1.1925 |
| C34 | 472 | 0.9140 | 1.35 | 0.00 | 0.1877 | 0.0000 | 0.1877 | 1.12 | 0.00238 | 0.29 | 1.2302 |
| C35 | 486 | 0.9170 | 1.06 | 0.00 | 0.1479 | 0.0000 | 0.1479 | 0.89 | 0.00182 | 0.22 | 0.9667 |
| C36 | 500 | 0.9190 | 1.11 | 0.00 | 0.1545 | 0.0000 | 0.1545 | 0.93 | 0.00185 | 0.23 | 1.0074 |
| C37 | 514 | 0.9220 | 0.92 | 0.00 | 0.1278 | 0.0000 | 0.1278 | 0.77 | 0.00149 | 0.18 | 0.8306 |
| C38 | 528 | 0.9240 | 0.92 | 0.00 | 0.1275 | 0.0000 | 0.1275 | 0.76 | 0.00145 | 0.18 | 0.8270 |
| C39 | 542 | 0.9260 | 0.80 | 0.00 | 0.1113 | 0.0000 | 0.1113 | 0.67 | 0.00123 | 0.15 | 0.7202 |
| C40 | 556 | 0.9280 | 0.76 | 0.00 | 0.1053 | 0.0000 | 0.1053 | 0.63 | 0.00113 | 0.14 | 0.6799 |
| C41 | 570 | 0.9300 | 0.68 | 0.00 | 0.0945 | 0.0000 | 0.0945 | 0.57 | 0.00099 | 0.12 | 0.6090 |
| C42 | 584 | 0.9310 | 0.63 | 0.00 | 0.0875 | 0.0000 | 0.0875 | 0.52 | 0.00090 | 0.11 | 0.5634 |
| C43 | 598 | 0.9330 | 0.50 | 0.00 | 0.0696 | 0.0000 | 0.0696 | 0.42 | 0.00070 | 0.08 | 0.4472 |
| C44 | 612 | 0.9350 | 0.45 | 0.00 | 0.0629 | 0.0000 | 0.0629 | 0.38 | 0.00062 | 0.07 | 0.4032 |
| C45+ | 719 | 1.1215 | 12.39 | 0.00 | 1.7216 | 0.0000 | 1.7216 | 10.32 | 0.01435 | 1.75 | 9.1972 |
| Total | | | 100.00 | 100.00 | 13.8938 | 2.7960 | 16.6898 | 100.00 | 0.82229 | 100.00 | 131.1116 |

TABLE 6B

Total reservoir fluid composition to C45+ - Plus Fraction Properties

| Component | Mole % | Grams | Moles | Volume | Mole Wt | Density |
|---|---|---|---|---|---|---|
| C7+ | 43.40 | 0.8003 | 0.35689 | 92.75092 | 224 | 0.8629 |
| C10+ | 30.56 | 0.6865 | 0.25130 | 77.46277 | 273 | 0.8862 |
| C12+ | 23.88 | 0.6097 | 0.19634 | 67.64994 | 311 | 0.9012 |
| C36+ | 3.01 | 0.1595 | 0.02471 | 15.28507 | 646 | 1.0437 |
| C45+ | 1.75 | 0.1032 | 0.01435 | 9.19720 | 719 | 1.1215 |

Exemplary Embodiments

An exemplary embodiment method for determining a composition of a fluid from a reservoir. The method includes depressurizing a single-phase fluid to atmospheric pressure to separate a gas phase from a liquid phase, recording the volume of the gas phase, determining the weight of the liquid phase, and determining an atmospheric gas-oil ratio (GOR) from the volume of the gas phase and the weight of the liquid phase. The method also includes determining the composition of the gas phase to C9+, measuring the density of the liquid phase, determining the molecular weight of the liquid phase, and determining the composition of the liquid phase to C45+. The total hydrocarbon composition of the fluid is calculated from the amount of the gas phase, the amount of the liquid phase, the composition of gas phase, the composition liquid phase, and the atmospheric GOR.

In an aspect, the method includes collecting a sample of the fluid from the reservoir in a sample container. In an aspect, the method includes pressurizing the sample container to form the single-phase fluid, and heating the sample container to about 100° C. In an aspect, the method includes pumping the single-phase fluid from the sample container into a flashing container, depressurizing the single-phase fluid during pumping forming the gas phase and the liquid phase, capturing the liquid phase in the flashing container, and capturing the gas phase in a flash gas cylinder.

In an aspect, a portion of the gas phase is recirculated through the liquid phase until equilibrium is reached between the gas phase and the liquid phase. In an aspect, the portion of the gas phase is recirculated through the liquid phase for about 5 minutes.

In an aspect, the method includes determining the weight of the liquid phase by measuring the weight of the flashing container.

In an aspect, the method includes determining the composition of the gas phase to C9+ using an extended gas chromatograph. In an aspect, the method includes determining amounts of non-hydrocarbons using a thermal conductivity detector in the extended gas chromatograph. In an aspect, the method includes determining amounts of hydrocarbons using a flame ionization detector.

In an aspect, the method includes determining the composition of the liquid phase to C45+ using high-resolution gas chromatography. In an aspect, the method includes using C14 as an internal standard.

In an aspect, the atmospheric GOR is calculated from the ratio of the gas phase and the liquid phase.

Another exemplary embodiment described in examples herein provides a method for measuring a composition of a reservoir fluid. The method includes pressurizing a sample container holding the reservoir fluid to form a single-phase fluid, pumping the single-phase fluid from the sample container into a separation oven, releasing pressure on the single-phase fluid in a flashing container to form a liquid phase and a gas phase, capturing the liquid phase in the flashing container, and flowing the gas phase through a gas collection cylinder into tubing in a gas accumulator oven. The method also includes recirculating a portion of the gas phase through the liquid phase at atmospheric pressure to equilibrate components in the gas phase and components in the liquid phase, and capturing a sample of the gas phase in the gas collection cylinder.

In an aspect, the method includes weighing the flashing container to determine the weight of the liquid phase. In an aspect, the method includes determining the density of the liquid phase.

In an aspect, the method includes determining the composition of the liquid phase to C45+ by high-resolution gas chromatography. In an aspect, the method includes determining the composition of the gas phase to C9+ by extended gas chromatography.

In an aspect, the method includes setting a separation oven temperature based on an API of the reservoir fluid. In an aspect, the method includes setting the separation oven temperature to about 20° C. for a reservoir fluid with an API between 25 and 60. In an aspect, the method includes setting the separation oven temperature to between 50° C. and 60° C.

Another embodiment described in examples herein provides a direct flash separator system. The direct flash separator system includes a separation oven. The separation oven includes a liquid flash container, a flash gas sample container, and a recirculation pump. The direct flash separator system also includes a gas accumulation oven. The gas accumulation oven includes a copper tubing line, a gas capture valve, and a digital gas meter.

In an aspect, the direct flash separator system includes a vacuum connection to purge the direct flash separator recirculation system. In an aspect, the direct flash separator system includes a helium connection to fill the direct flash separator recirculation system with helium. In an aspect, the direct flash separator system includes a two-way valve to allow the liquid flash container to be coupled to an inlet line or to be coupled to a gas recirculation line.

Other implementations are also within the scope of the following claims.

What is claimed is:

1. A method for determining a composition of a fluid from a reservoir, comprising:
    collecting a sample of the fluid from the reservoir in a sample container;
    pressurizing the sample container to form the single-phase fluid;
    heating the sample container to about 100° C.;
    pumping the single-phase fluid from the sample container into a flashing container;
    depressurizing the single-phase fluid during pumping forming a gas phase and a liquid phase;
    capturing the liquid phase in the flashing container;
    capturing the gas phase in a flash gas cylinder;
    recirculating a portion of the gas phase through the liquid phase until equilibrium is reached between the gas phase and the liquid phase;
    recording a volume of the gas phase;
    determining a weight of the liquid phase;
    determining an atmospheric gas-oil ratio (GOR) from the volume of the gas phase and the weight of the liquid phase;
    determining composition of the gas phase to C9+;
    measuring density of the liquid phase;
    determining molecular weight of the liquid phase;
    determining composition of the liquid phase to C45+; and
    calculating the total hydrocarbon composition of the fluid from:
        the volume of the gas phase;
        the weight of the liquid phase;
        the composition of the gas phase;
        the composition of the liquid phase; and
        the atmospheric GOR.

2. The method of claim 1, comprising recirculating the portion of the gas phase through the liquid phase for about 5 minutes.

3. The method of claim 1, comprising determining the weight of the liquid phase by measuring the weight of the flashing container.

4. The method of claim 1, comprising determining the composition of the gas phase to C9+ using an extended gas chromatograph.

5. The method of claim 4, comprising determining amounts of non-hydrocarbons using a thermal conductivity detector in the extended gas chromatograph.

6. The method of claim 4, comprising determining amounts of hydrocarbons using a flame ionization detector.

7. The method of claim 1, comprising determining the composition of the liquid phase to C45+ using high-resolution gas chromatography.

8. The method of claim 7, comprising using C14 as an internal standard.

9. The method of claim 1, wherein the atmospheric GOR is calculated from the ratio of the gas phase and the liquid phase.

* * * * *